United States Patent
Abraham et al.

[11] Patent Number: 6,052,249
[45] Date of Patent: Apr. 18, 2000

[54] METHOD AND APPARATUS FOR DATA STORAGE USING THERMAL PROXIMITY IMAGING

[75] Inventors: David William Abraham, Ossining; Anthony Paul Praino, Poughquaq, both of N.Y.; Mark Edward Re, Los Gatos, Calif.; Hemantha Kumar Wickramasinghe, Chappaqua, N.Y.

[73] Assignee: International Business Machines Corporation, Armonk, N.Y.

[21] Appl. No.: 09/129,547

[22] Filed: Aug. 5, 1998

Related U.S. Application Data

[62] Division of application No. 08/636,384, Apr. 23, 1996, Pat. No. 5,850,374, which is a division of application No. 08/056,164, Apr. 30, 1993, Pat. No. 5,527,110.

[51] Int. Cl.$^7$ ....................................................... G11B 5/09
[52] U.S. Cl. .................................. 360/59; 369/14
[58] Field of Search .................. 360/31, 59, 114; 369/53, 14, 13, 110, 15; 374/5, 7, 141, 120, 164, 137

[56] References Cited

U.S. PATENT DOCUMENTS

| | | |
|---|---|---|
| 3,416,373 | 12/1968 | Havens . |
| 3,716,845 | 2/1973 | Chaffin, III ............................. 365/120 |
| 3,795,133 | 3/1974 | Fergason et al. ........................... 374/7 |
| 3,808,439 | 4/1974 | Renius ........................................ 374/4 |
| 4,430,010 | 2/1984 | Zrenner et al. ............................. 374/5 |
| 4,468,136 | 8/1984 | Murphy et al. ......................... 374/124 |
| 4,513,384 | 4/1985 | Rosencwaig ................................ 374/7 |
| 4,522,510 | 6/1985 | Rosencwaig et al. ...................... 374/7 |
| 4,532,802 | 8/1985 | Yeack-Scranton et al. . |
| 4,671,674 | 6/1987 | Detronde ..................................... 374/5 |
| 4,679,945 | 7/1987 | Rosencwaig et al. ...................... 374/7 |
| 4,747,698 | 5/1988 | Wickramasinghe et al. .............. 374/6 |
| 4,762,427 | 8/1988 | Hori et al. ............................... 374/141 |
| 4,777,544 | 10/1988 | Brown et al. ............................. 360/75 |
| 4,853,810 | 8/1989 | Pohl et al. . |
| 4,854,730 | 8/1989 | Fraden .................................... 374/164 |
| 4,886,370 | 12/1989 | Koshihara et al. ......................... 374/5 |
| 4,931,887 | 6/1990 | Hegde et al. ............................. 360/75 |
| 5,031,456 | 7/1991 | Askwith et al. ............................ 374/5 |
| 5,054,936 | 10/1991 | Fraden .................................... 374/164 |
| 5,130,866 | 7/1992 | Klassen et al. ........................... 360/75 |
| 5,408,365 | 4/1995 | Van Doorn et al. ...................... 360/46 |
| 5,455,730 | 10/1995 | Dovek et al. ............................ 360/113 |
| 5,523,898 | 6/1996 | Jove et al. ................................. 360/66 |
| 5,527,110 | 6/1996 | Abraham et al. ........................... 374/7 |
| 5,650,887 | 7/1997 | Dovek et al. ............................. 360/75 |

FOREIGN PATENT DOCUMENTS

| | | | |
|---|---|---|---|
| 0139462 | 1/1980 | Germany | ................... 374/4 |

OTHER PUBLICATIONS

R.E. Fontana, Jr., D.E. Horne and H. Sussner, "Disk Asperity Detector" Aug. 1983, IBM Technical Disclosure Bulletin, vol. 26, No. 3A, pp. 1278–1280.

R.E. Fontana, Jr., D.E. Horne and H. Sussner, "Disk Asperity Detector" Aug. 1983, IBM Technical Disclosure Bulletin vol. 26 No. 3A pp. 1278–1280.

"Disk Asperity Detector," IBM Technical Disclosure Bulletin, vol. 26, No. 3A, Aug. 1993.

*Primary Examiner*—Tan Dinh
*Attorney, Agent, or Firm*—Heslin & Rothenberg, P.C.

[57] ABSTRACT

A method and apparatus for accessing a data storage medium having raised and lowered portions indicative of data stored on the medium. Energy is supplied to a sensor which is moved relative to, and in close proximity to, a surface of the medium on which the data in the form of raised and lowered portions is stored. The sensor and the storage medium are moved in relation thereto, such that the sensor remains at a substantially constant fly spacing therefrom. A decrease in temperature of the sensor is detected when it is in proximity to a variation, i.e., a raised portion on the medium. This detected decrease in temperature associated with a raised variation, e.g., asperity, can be used as the basis upon which to detect the data on the data storage medium. The data storage medium may also contain magnetically stored data, such that the surface variations and the magnetic characteristics of the data storage medium can both be utilized to store data thereon.

22 Claims, 5 Drawing Sheets

METHOD AND APPARATUS FOR DATA STORAGE USING THERMAL PROXIMITY IMAGING

CROSS-REFERENCE TO RELATED APPLICATIONS

This application is a divisional of U.S. patent application Ser. No. 08/636,384, filed Apr. 23, 1996, now U.S. Pat. No. 5,850,374, entitled "METHOD AND APPARATUS FOR DATA STORAGE USING THERMAL PROXIMITY IMAGING," which application itself is a divisional of U.S. patent application Ser. No. 08/056,164, filed Apr. 30, 1993, now U.S. Pat. No. 5,527,110, issued Jun. 18, 1996 and entitled "METHOD AND APPARATUS FOR THERMAL PROXIMITY IMAGING."

BACKGROUND OF THE INVENTION

1. Technical Field

This invention relates generally to a method and an apparatus for mapping the topography of a surface. More particularly it relates to a method and apparatus for detecting small defects by detecting the presence and nature of these defects using thermal conduction. More specifically, it relates to a method and apparatus for analyzing the surface of a rotating disk in a direct access storage device, such as a magnetic disk drive.

2. Background Art

In data processing systems, magnetic disk drives are often used as direct access storage devices. In such devices, read-write heads are used to write data on or read data from an adjacently rotating hard or flexible disk. To prevent damage to either the disk or the read-write head, it has been recognized for a long time that the surface of the disk should be very flat and free of any bumps or the like which might be contacted by the read-write head. Also, the read-write heads have been designed so that they will fly over the surface of the rotating disk at a very small, though theoretically constant distance above the disk, the separation between the read-write head and the disk being maintained by a film of air. During its flight, the head undergoes continuous vibration, pitch and roll as the topography of the disk changes beneath the head. If the quality of the disk or the read-write head is poor, occasional rubbing or sharp contact may occur between the disk and the read-write head, leading Lo damage to the head or to the disk, or loss of valuable data, or all of these.

Various attempts have been made to provide increased assurance that such undesirable contact between a read-write head and a recording disk does not occur. Rigid manufacturing and quality assurance specifications for both the recording disk and the read-write head have been instituted.

Disk inspection for various types of defects, including magnetic, optical and topographic (i.e., delamination, voids inclusions, asperities, etc.) is of critical importance for the increasingly stringent production requirements facing a manufacturer today as smaller drives store more data. Many methods of inspection to find defects are in use, and many more have been proposed. These include optical techniques (fiber interferometry, bulk optic shear interferometry, microISA), magnetic readout (simply screening, HRF, etc.,) and mechanical testing ( the so-called PZT glide test, described below). Each of these techniques may play a role in achieving the goal of the virtually defect free production of magnetic disks. However, with a tightening market and more exacting technical requirements as heads fly lower and faster, less expensive and more accurate inspection schemes become more significant.

The PZT glide test is disclosed in U.S. Pat. No. 4,532,802 to Yeack-Scranton et al. A read-write head is provided with a plurality of piezo-electric transducers which produce signals related to its movement as it flies over an adjacently rotating recording disk. By filtering these signals to determine their spectral components in low, medium and high ranges, hard contacts between the head and disk, disk wear or roughness and head movement can be determined. While quite satisfactory in many respects, this technique depends on contact between the read-write head and the disk, and as a result the heads wear out and costly replacement is required. In addition, resolution in the radial direction is limited by the geometry of the head to about 2 mm in the radial direction.

U.S. Pat. No. 4,747,698 to Wickramasinghe et al is directed to a Scanning Thermal Profiler. A fine scanning tip is heated to a steady state temperature at a location remote from the structure to be investigated. Thereupon, the scanning tip is moved to a position proximate to, but spaced from the structure. At the proximate position, the temperature variation from the steady state temperature is detected. The scanning tip is scanned across the surface structure with the aforesaid temperature variation maintained constant. Piezo electric drivers move the scanning tip both transversely of, and parallel to, the surface structure. Feedback control assures the proper transverse positioning of the scanning tip and voltages thereby generated replicate the surface structure to be investigated. While this approach provides excellent depth resolution, it requires the use of an expensive scanning tip. It also has, in common with the approach illustrated in U.S. Pat. No. 4,532,802 discussed above, the disadvantage that it cannot readily be utilized on an assembled disk drive.

SUMMARY OF THE INVENTION

It is a principal object of the invention to provide a method and an apparatus for the mapping of asperities on a relatively smooth surface by thermal proximity imaging.

It is a further object of the invention to provide a method and an apparatus for doing this mapping at low cost.

It is an additional object of the invention to provide a method for storing data in the form of mechanical features on a smooth surface and retrieving the data by thermal proximity imaging.

It is yet another object of the invention to do thermal proximity imaging without contacting the asperities on a relatively smooth surface.

It is still another object of the invention to provide a method and apparatus for performing thermal proximity imaging while keeping the distance between the thermal proximity sensor and the relatively smooth surfaces essentially constant.

The present invention provides a method for mapping the character and location of small surface variations on a planar surface. The method comprises the steps of supplying energy to an object in close proximity to the planar surface thereby raise the temperature of the object; moving the object with respect to the planar surface while keeping the distance from the planar surface substantially constant; and detecting a decrease in temperature of the object when it is in proximity to the variation to define the location and character of the variation. The energy supply may be thermal energy or optical energy but preferably is electrical energy which heats a resistive element. Preferably, the object is the magnetoresistive head of a disk drive assembly. The change in temperature is detected by monitoring the resistance of the magnetoresistive sensor of the head. The energy may be supplied in pulses to obtain higher peak temperatures while avoiding mechanical distortion of the object. It is preferred that the object be positioned with respect to the surface so that when that relative motion between the surface and the object occurs, the object does not contact the surface.

The present invention is also directed to an apparatus for detecting the presence of height variations on a substantially planar surface. The apparatus comprises an object to be placed in close proximity to the planar surface; energy means for supplying energy to the object to thereby raise its temperature; means for moving the object with respect to the planar surface so as to maintain the object at a substantially constant distance therefrom; and means for detecting a drop in temperature of the object when it is in proximity to a variation. The energy means may supply thermal or optical energy, but preferably supplies electrical energy to heat the object. The object may be the magnetoresistive head of the disk drive assembly which receives electrical energy. The detecting means detects a change in temperature by monitoring the resistance of the magnetoresistive sensor of the head. Preferably the energy is pulsed in order to obtain higher peak temperatures and yet avoid mechanical distortion of the object. It is preferred that the object be positioned during use of the apparatus so that that it does not contact the surface or the variations in the surface during relative motion of the surface with respect to the object.

DETAILED DESCRIPTION OF THE PREFERRED EMBODIMENT

Figure 1:
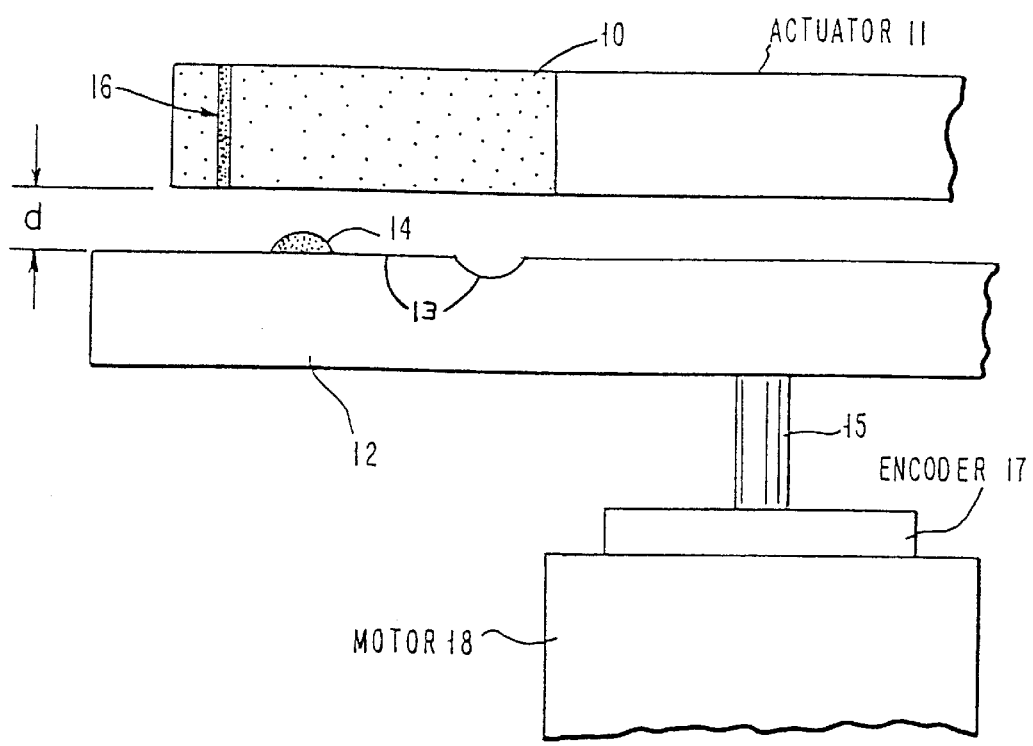
FIG. 1 is an enlarged, schematic view of a read-write head flying over a rotating disk having an asperity thereon.

Referring to FIG. 1 a standard magnetoresistive (MR) head or slider 10 mounted on an actuator 11 is used to detect disk asperities. The geometry of the slider 10 with relation to the disc 12 and exemplary lowered portion 13 and raised portion 14 (e.g. asperity) are illustrated. As is well known in the art, disk 12 rotates on a spindle 15, driven by a motor 18. An encoder 17 provides data on the relative rotational orientation of disk 12 with respect to slider 10.

Slider 10 is designed to provide a constant fly height (for a given rotational disk speed) of slider 10 above the surface of disk 12. The head temperature is elevated using Joule heating of the MR element or stripe 16. As the head passes over the disk it reaches some elevated temperature determined by the heat load and by geometry and thermal considerations. If a particle causes the gap spacing to temporarily vary, the temperature of the stripe will drop and can be sensed as a momentary spike in the head readout signal due to the non-zero temperature coefficient of resistance. The amplitude of the spike is proportional to the temperature differential maintained in the MR head versus the disk surface and to the thermal properties of the asperity, and depends roughly as 1/d where d is the head-disk spacing (as opposed to the roughly average fly height).

Even in standard operation, the MR stripe 16 can be expected to run quite hot, since typical bias currents are on the order of 10 mA, with head resistances of a few tens of ohms. Thus, in a head/slider weighing no more than a gram, tens of milliwatts in Joule heating occurs. The temperature rise can be expected to be significant, and in fact proportional to the square of the current. The temperature rise will be determined by this heat flow, balanced by convective and/or conductive losses into the atmosphere and the disc. Further heating can be supplied with a resistor, and in fact may be desirable in order to bias the magnetic sensitivity to near zero. Typically, MR heads have a thermal sensitivity of resistance of $3\times10^{-3}$/K. By avoiding substantial bias at the frequency used to measure the resistance of the head, magnetic contributions can be nearly eliminated.

Particle size can be estimated from the strength of the thermal signal. The effectiveness of cooling depends on both the width and height of the particle (or void), and during the scan past the defect a fixed amount of heat energy will flow to the disk surface.

Use of existing MR head technology has several advantages. First, no additional development need be done, and implementation in a test stand can be achieved with little extra cost. Second, a large knowledge base exists about MR head properties, so that complete understanding of thermal response versus magnetic properties can be had at small added effort. Third, no modification of the head is required, so that significant costs in replacement heads is avoided (as exists with the PZT glide tester described in U.S. Pat. No. 4,532,802). Fourth, topographic screens and magnetic evaluation can be performed nearly simultaneously (i.e., sequentially), which is important as a time saver, and for providing new information correlating the two properties. Fifth, this technique can provide higher resolution and less ambiguous information about asperities than piezo-based methods. Finally, the technique can be used to evaluate disks in assembled head-disk assemblies of disk drives.

Figure 2:
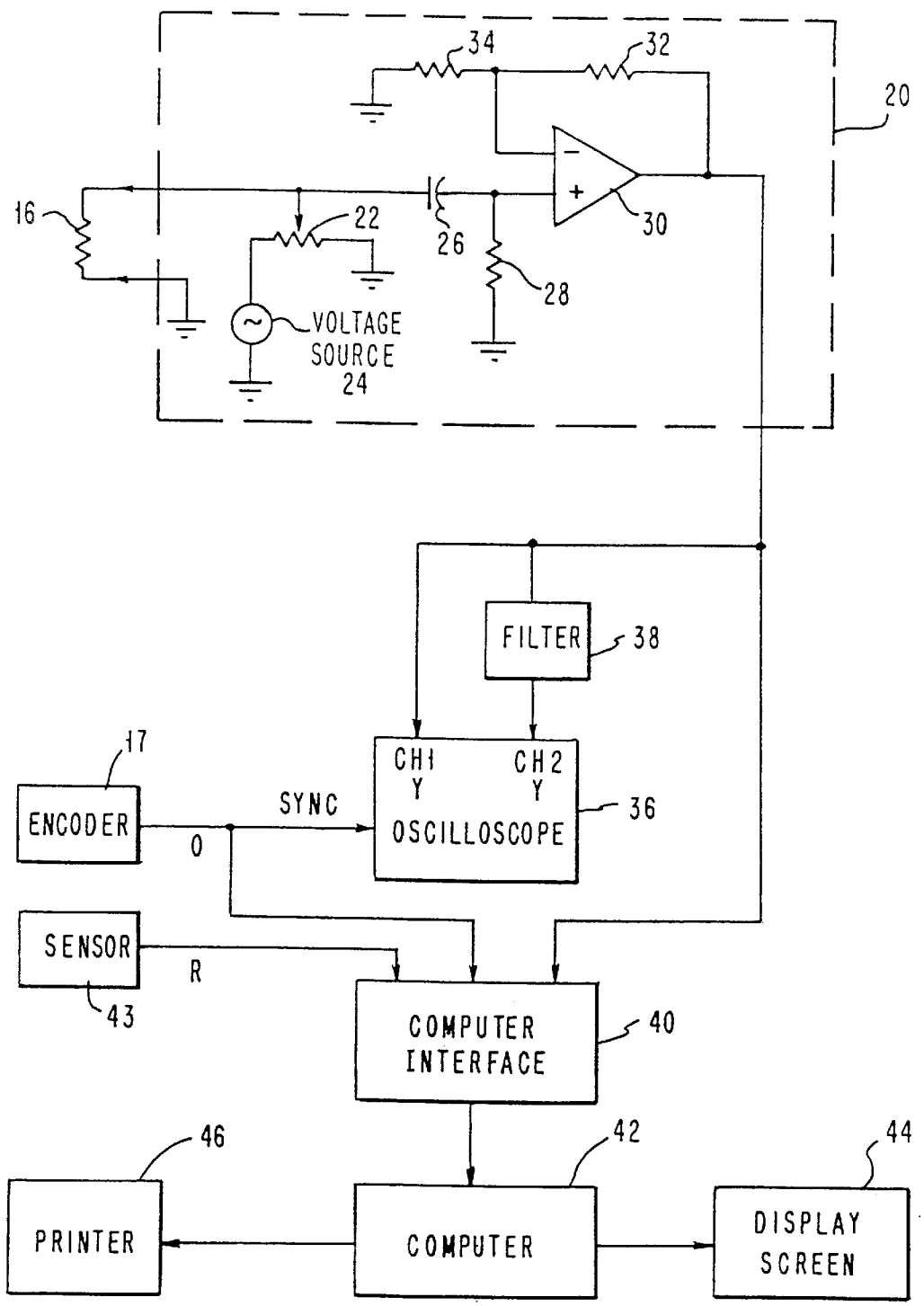
FIG. 2 is a diagram, partially schematic and partially in block, of an apparatus according to the invention.

Referring to FIG. 2, a system for obtaining and evaluating data from slider 10 is illustrated. A pre-amplifier circuit 20 provides a bias current to the MR sensor object 16 of slider 10 (FIG. 1). A potentiometer 22 connected to a voltage source 24 at one end and ground at the other end permits adjustments of the bias current. The slider of the potentiometer is connected to one side of MR sensor object 16 of slider 10. The other side of MR sensor object 16 is connected to ground, as is the side of voltage source 24 not connected to potentionmeter 22.

Voltage source 24 may supply direct current, alternating current, or pulses having one polarity or alternating polarities. For the highest sensitivity, and therefore the best resolution of height of an asperity, pulses are preferred. Pulsed operation permits the highest peak temperatures without overheating the slider 10 so as to cause mechanical distortion thereof.

Capacitor 26 and resistor 28 form a high pass filter which passes signals from the slider 10 to the non-inverting input of an operational amplifier 30. Resistor 32 connected from the output of the operational amplifier to the inverting input and resistor 34 connected from the inverting input to ground determine the gain of operational amplifier 30, in a manner well known in the art. Typically, resistors 32 and 34 are selected so that operational amplifier 30 has a gain of 500.

Output signals from amplifier 30 are provided as Y axis inputs to a first channel of an oscilloscope 36. The same signals are sent to a high pass filter 38 and then to a Y axis input of a second channel of oscilloscope 36. The signals from a small asperity on the disk are generally in the form of a sharp spike having a 3 dB width corresponding to a time of less than 50 microseconds, or typically less than 250 microns of disk travel. These spikes are displayed on the first channel of oscilloscope 36. The magnetic data, which typically changes amplitude much more rapidly, passes through filter 38 and may be viewed on the second channel of the oscilloscope 36.

The signals from amplifier 30 are also supplied to a computer interface 40 which includes an analog-to-digital converter, of a type well known in the art, which converts the analog signals from operational amplifier 30 to digital form, for acquisition by a computer 42.

Information concerning the rotational position of the slider 10 with respect to the disk, provided by shaft encoder 17, which may be a pulse for every revolution of disk 12 is used as a synchronization input to oscilloscope 36. It is also used as a so-called 0 position input. It is therefore supplied to computer interface 40 for eventual use by computer 42. The position of slider 10 in the radial direction with respect to disk 12, is determined by a head position sensor 43 associated with the actuator 11. This radial position information is also supplied to computer interface 40.

The information supplied to computer interface 40 provides three dimensional data where the 0 and radial position data define the position of an asperity on the disk 12, while the information derived from the output of amplifier 30 provides an indication concerning the severity of the asperity, with respect to height. The information is stored in a data base in computer 42, processed by suitable processing techniques and finally displayed on a display screen 44. Alternatively, a hard copy print out is provided by a printer 46.

Figure 3A:
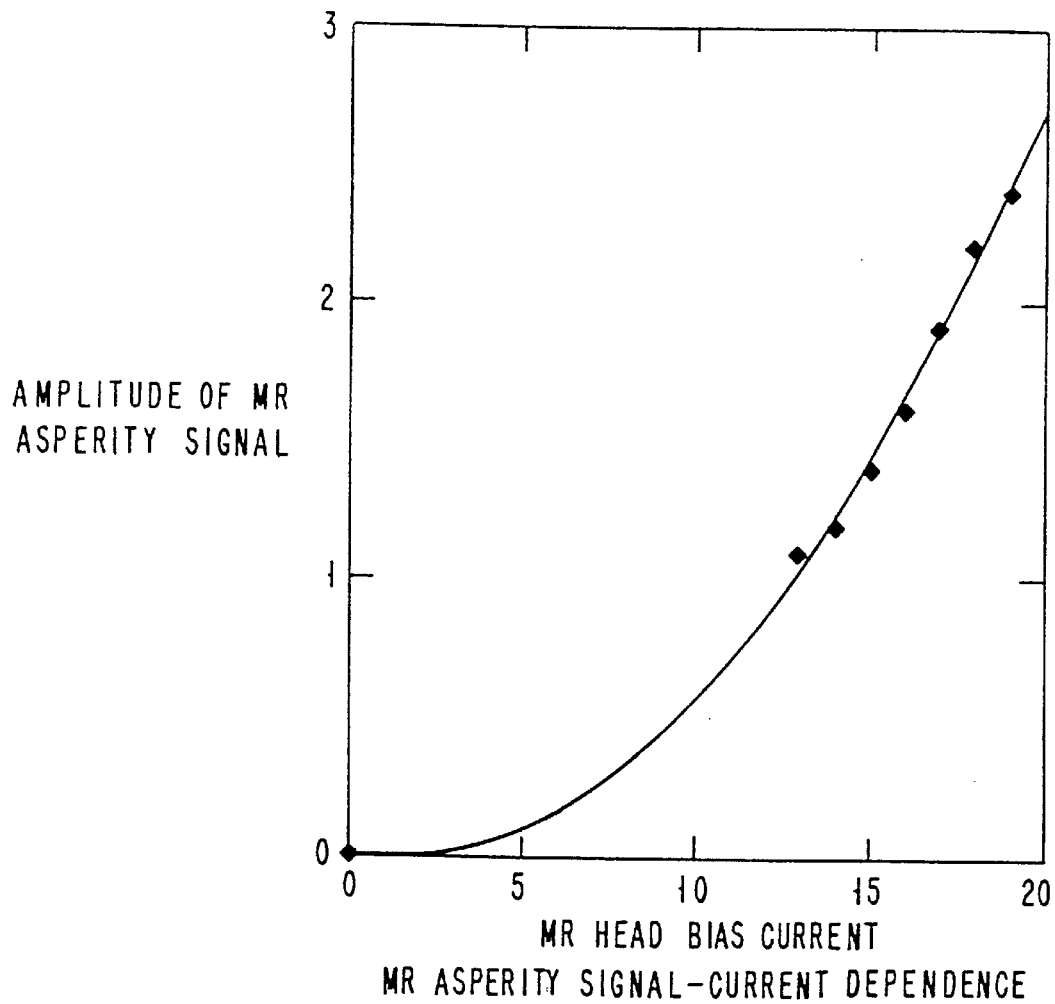
FIG. 3A is a plot of the amplitude of the signal from an asperity versus the bias current to the magnetoresistive head.

FIG. 3A, is a plot of the thermal signal output from a defect as a function of current. The amplitude is parabolic in current and suggests that the amplitude of the signal is proportional to the power dissipated in the head and therefore to the temperature difference between the slider 10 and the disk 12.

Figure 3B:
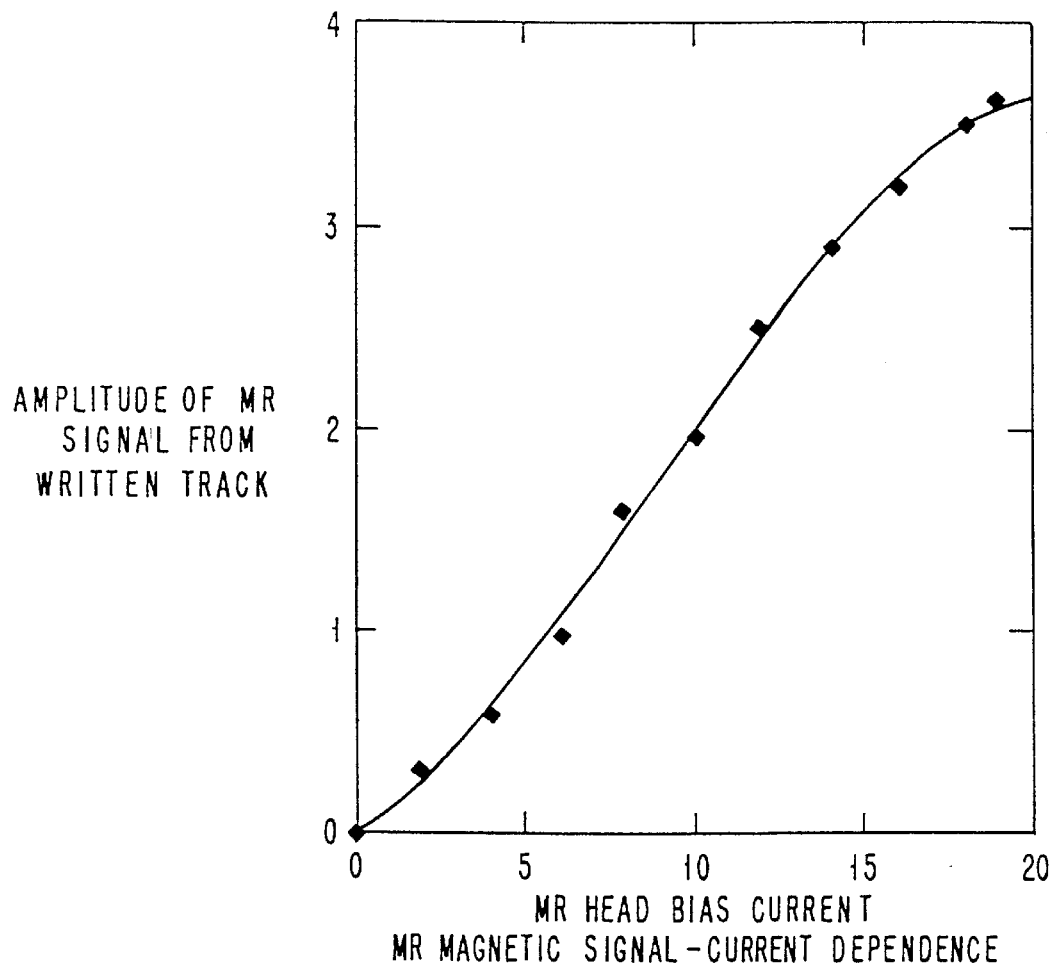
FIG. 3B is a plot of the amplitude of a read back signal from a written magnetic track versus the bias current to the magnetoresistive head.

FIG. 3B, illustrates the MR read signal amplitude from a written track on a disk. The "S" shape is characteristic of the MR head showing increased sensitivity with current into a linear region, followed by saturation at high current. Thus "magnetic contrast" or the influence of magnetic domains may be separated from the topographic information by operating at two different currents. Alternatively by using an AC current and observing the signals produced at the second harmonic, magnetic contrast can be removed. Since magnetic signal strength is nominally linear with respect to MR bias current, magnetic and thermal information can be separated in the following way: Instead of using a DC bias, a current at some frequency fo is provided. Then any signal measured from the MR element at a frequency 2fo is due to the thermal variations and not to magnetic information.

Further, the shape of the signals produced is quite different. Small asperities produce a characteristic spike shape, as noted above, while magnetic variations on the surface of the disk produce extended width signals. Thus, filtering, as described above, is also a method of distinguishing magnetic signals from thermal signals.

Figure 4A:
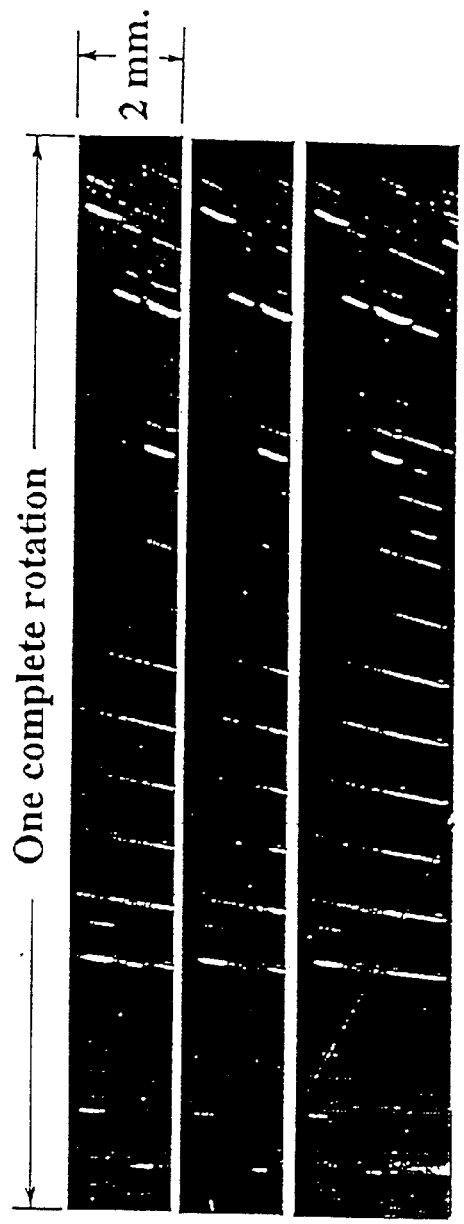
FIG. 4A is a thermal proximity image produced using the apparatus of FIG. 2.
Figure 4B:
FIG. 4B is an enlargement of a portion of the image of FIG. 4.

FIG. 4A, is a thermal proximity image produced by a method and apparatus according to the invention. FIG. 4B, is an enlarged view of the lower right hand corner of FIG. 4A. The disk used to make the images was made of aluminum with no magnetic layer deposited thereon. However, the disk was carbon coated and a lubrication coating was applied. The array of lines that can be seen on the disk were provided by a lithography technique. These lines have a width of between 10 and 100 microns, and heights between 200 and 800 Å.

The light regions are unintended asperities having widths of approximately 100 microns and heights above 800 Å.

It is contemplated that with an improved, specially designed sensor and an improved system for data acquisition and analysis, resolution in the circumferential direction can be improved to be in the range of 2 to 5 um. With respect to height, the Johnson noise limits the resolution to below one Å. for a bandwidth of 1 MHz.

While the description of the invention set forth above has centered primarily on the mapping and characterization of asperities, it is noted that the invention may also be applied to a method and apparatus for the storage of information. In particular, information can be encoded into the surface of a disk in the form of small raised (FIG. 1, asperity 14) or lowered (FIG. 1, reference 13) portions. Using the thermal imaging method and apparatus described herein, the information can be read back and retrieve for use in, for example, a data processing system. Further, in view of the ability to discriminate between magnetic signals and signals resulting from the topography of the disk, it is possible to encode some information on the disk using magnetic techniques and other information using topographical techniques. Different kinds of information can be encoded in this manner as, for example, it may be preferable to encode information to be permanently stored by topographical techniques while information which is to be changed can be encoded by magnetic techniques.

While the invention has been particularly shown and described with respect to a preferred embodiment thereof, it will be understood by those skilled in the art that changes in form and details may be made therein without departing from the scope and spirit of the invention.

What is claimed is:

1. A method for storing data on a medium, the data to be accessed by monitoring a thermal environment between the medium and a sensor spaced therefrom and in motion relative thereto, the method comprising:

encoding data onto the medium in the form of raised and lowered portions thereon, the raised and lowered portions affecting the thermal environment between the medium and the sensor.

2. The method of claim 1, further comprising:

placing the medium in motion relative to the sensor;

monitoring the thermal environment between the medium and the sensor; and ascertaining the encoded data using the monitored thermal environment.

3. The method of claim 2, wherein the raised and lowered portions on the medium change the monitored thermal environment by changing the spacing between the sensor and the medium, and wherein the ascertaining includes detecting the changes in the monitored thermal environment.

4. The method of claim 2, wherein said placing includes flying the sensor over a surface of the medium at a substantially constant reference fly height.

5. The method of claim 4, wherein a reference temperature of the monitored thermal environment is a function of the reference fly height.

6. The method of claim 5, wherein upon encountering one of a raised portion and a lowered portion with the sensor, a change in the reference fly height and therefore the reference temperature of the monitored thermal environment occurs.

7. The method of claim 6, wherein said ascertaining includes detecting the change in the reference temperature of the monitored thermal environment and therefore the change in the reference fly height.

8. The method of claim 6, wherein the medium comprises a substantially planar portion and the lowered portions of the medium comprise the substantially planar portion and are therefore associated with the reference fly height and reference temperature.

9. The method of claim 8, wherein the raised portions of the medium comprise protrusions rising above the substantially planar portion of the medium.

10. The method of claim 9, wherein the change in the reference temperature of the monitored thermal environment comprises a decrease in temperature corresponding to a decrease in spacing between the sensor and an encountered one of the protrusions, and wherein the ascertaining includes detecting the decrease in temperature.

11. The method of claim 2, further comprising:

setting a temperature of the sensor to a predetermined value to facilitate said monitoring.

12. The method of claim 2, further comprising:

magnetically storing data on the medium.

13. A method for reading data from a medium in motion relative to a sensor, comprising:

monitoring a thermal environment between the medium and the sensor, the thermal environment being representative of a spacing between the sensor and the medium; and reading data from the medium including detecting changes in the monitored thermal environment and therefore changes in the spacing, the changes in the spacing corresponding to raised and lowered portions on the medium representative of said data.

14. The method of claim 13, wherein said monitoring includes flying the sensor over the medium at a reference fly height, the reference fly height corresponding to a reference temperature of the monitored thermal environment.

15. The method of claim 14, wherein said reading includes detecting a change in the reference temperature and therefore a change in the reference fly height corresponding to one of the raised and lowered portions.

16. The method of claim 13, wherein the lowered portions correspond to a substantially planar portion of the medium.

17. The method of claim 16, wherein the raised portions correspond to protrusions rising above the substantially planar portion of the medium.

18. The method of claim 13, further comprising:

reading magnetically stored data from the medium.

19. A data storage medium for use in a data storage system wherein the medium is accessed by monitoring a thermal environment between the medium and a sensor spaced therefrom and in motion relative thereto, the medium having raised and lowered portions thereon representing data stored on the medium to be sensed by said sensor, the raised and lowered portions affecting the thermal environment between the medium and the sensor.

20. The storage medium of claim 19, wherein the raised portions comprise protrusions rising above a substantially planar surface of the medium.

21. The storage medium of claim 20, wherein the lowered portions comprise the substantially planar surface.

22. The storage medium of claim 19, wherein the medium includes data magnetically stored thereon.

* * * * *